United States Patent [19]

Shimada et al.

[11] Patent Number: 5,434,028
[45] Date of Patent: Jul. 18, 1995

[54] DIAMINE COMPOUNDS

[75] Inventors: Tomoyuki Shimada, Shizuoka; Masaomi Sasaki, Susono; Chiaki Tanaka, Shizuoka, all of Japan

[73] Assignee: Ricoh Company, Ltd., Tokyo, Japan

[21] Appl. No.: 304,553

[22] Filed: Sep. 12, 1994

Related U.S. Application Data

[63] Continuation of Ser. No. 202,238, Feb. 25, 1994.

[30] Foreign Application Priority Data

Feb. 26, 1993 [JP] Japan .................................. 5-062773
Jun. 15, 1993 [JP] Japan .................................. 5-168515
Aug. 9, 1993 [JP] Japan .................................. 5-217030
Dec. 7, 1993 [JP] Japan .................................. 5-340078

[51] Int. Cl.$^6$ ...................... G03G 15/02; C07C 69/96
[52] U.S. Cl. ...................................... 430/59; 558/269
[58] Field of Search .......................... 558/269; 430/59

*Primary Examiner*—José G. Dees
*Assistant Examiner*—Joseph M. Conrad, III
*Attorney, Agent, or Firm*—Oblon, Spivak, McClelland, Maier, & Neustadt

[57] ABSTRACT

A diamine compound having formula (I):

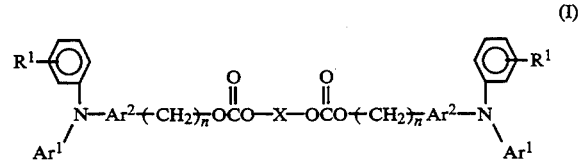

wherein $R^1$ is hydrogen, an alkyl group having 1 to 6 carbon atoms which may have a substituent, an alkoxyl group having 1 to 6 carbon atoms which may have a substituent, an aryl group which may have a substituent, or an alkenyl group having 1 to 6 carbon atoms which may have a substituent; $Ar^1$ is an aryl group which may have a substituent; $Ar^2$ is a bivalent group selected from the group consisting of an arylene group and a stilbene group, which may have a substituent; n is an integer of 0 to 2; and X is a group selected from the group consisting of:

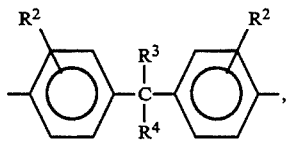

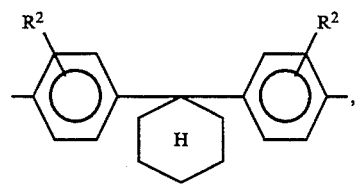

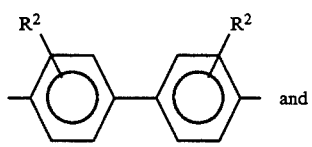

and

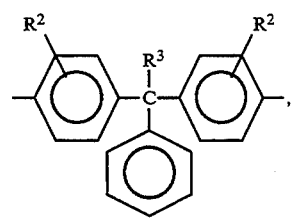

in which $R^2$ is hydrogen, an alkyl group having 1 to 6 carbon atoms which may have a substituent, an aryl group or a halogen; $R^3$ and $R^4$ each is an alkyl group having 1 to 6 carbon atoms or an aryl group. The diamine compounds are useful as charge transport materials in electrophotographic photoconductor applications, particularly layered photoconductors comprising a charge generation layer containing a pigment as a charge generating material, and a charge transport layer containing the diamine as a charge transport material.

9 Claims, 12 Drawing Sheets

DIAMINE COMPOUNDS

REFERENCE TO RELATED APPLICATION

This application is a Continuation of application Ser. No. 08/202,238, filed Feb. 25, 1994.

BACKGROUND OF THE INVENTION

1. Field of the Invention

The present invention relates to diamine compounds useful as organic photoconductive materials for use in electrophotography.

2. Discussion of Background

Conventionally, a variety of organic photoconductive materials such as poly-N-vinylcarbazole and triphenylamine compounds (U.S. Pat. No. 3,180,730); and benzidine compounds (U.S. Pat. No. 3,265,496, Japanese Patent Publication 39-11546 and Japanese Laid-Open Patent Application 53-27033) are proposed to use in a photoconductor for use with the electrophotographic process.

The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electrical charge of the exposed areas, so that a latent electrostatic image is formed on the photoconductor. The thus formed latent electrostatic image is developed to a visible image by toner particles.

Fundamental characteristics required for the photoconductor for use in such an electrophotographic process are: (1) chargeability to an appropriate potential in the dark, (2) minimum dissipation of electrical charge in the dark, and (3) rapid dissipation of electrical charge when exposed to light.

However, while the above-mentioned conventional organic photoconductive materials have many advantages, they cannot satisfy all the aforementioned electrophotographic requirements.

SUMMARY OF THE INVENTION

It is therefore an object of the present invention is to provide novel diamine compounds serving as photoconductive materials for use in an electrophotographic photoconductor, which can meet all of the above-mentioned fundamental electrophotographic characteristics.

The object of the present invention can be achieved by a diamine compound of formula (I):

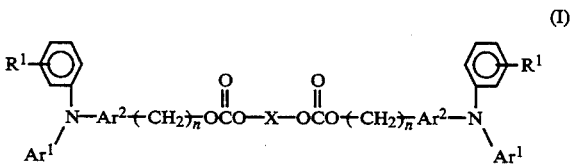

wherein $R^1$ is hydrogen, an alkyl group having 1 to 6 carbon atoms which may have a substituent, an alkoxyl group having 1 to 6 carbon atoms which may have a substituent, an aryl group which may have a substituent, or an alkenyl group having 1 to 6 carbon atoms which may have a substituent; $Ar^1$ is an aryl group which may have a substituent; $Ar^2$ is a bivalent group selected from the group consisting of an arylene group and a stilbene group, which may have a substituent; n is an integer of 0 to 2; and X is a group selected from the group consisting of:

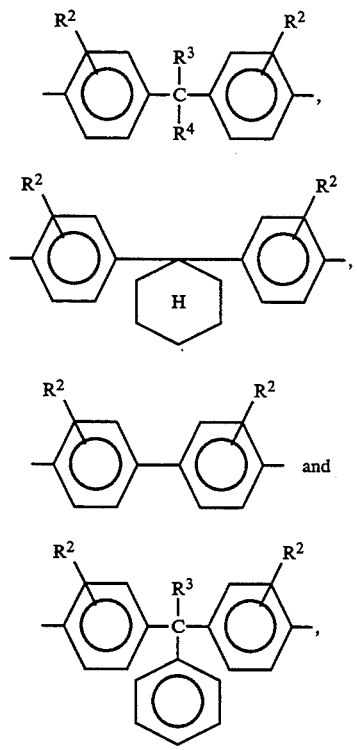

in which $R^2$ is hydrogen, an alkyl group having 1 to 6 carbon atoms which may have a substituent, an aryl group or a halogen; $R^3$ and $R^4$ each is an alkyl group having 1 to 6 carbon atoms or an aryl group.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
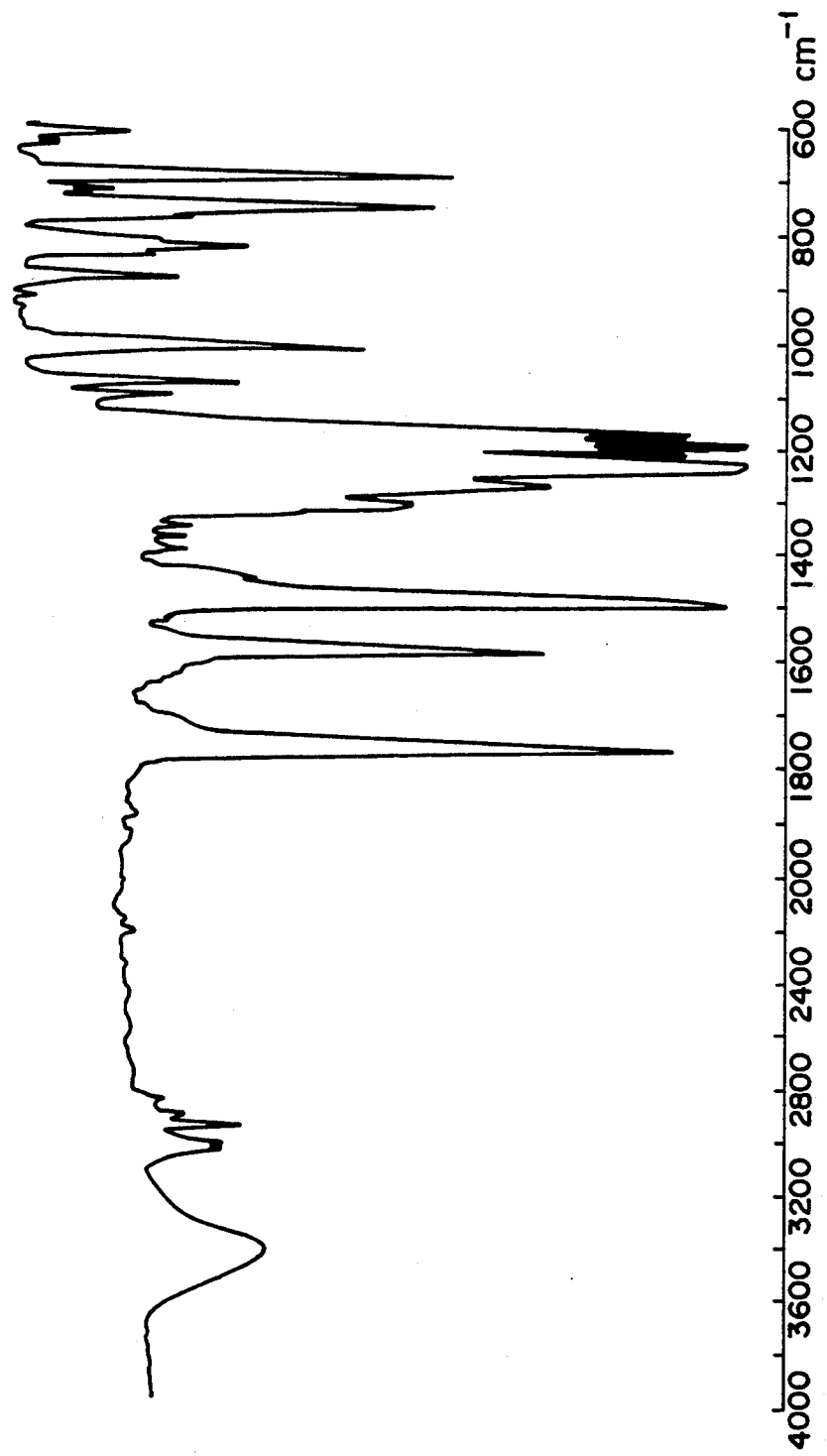
FIGS. 1 through 12 are IR spectra, using a KBr tablet, of diamine compounds according to the present invention which are respectively obtained in Examples 1 to 12.
Figure 2:
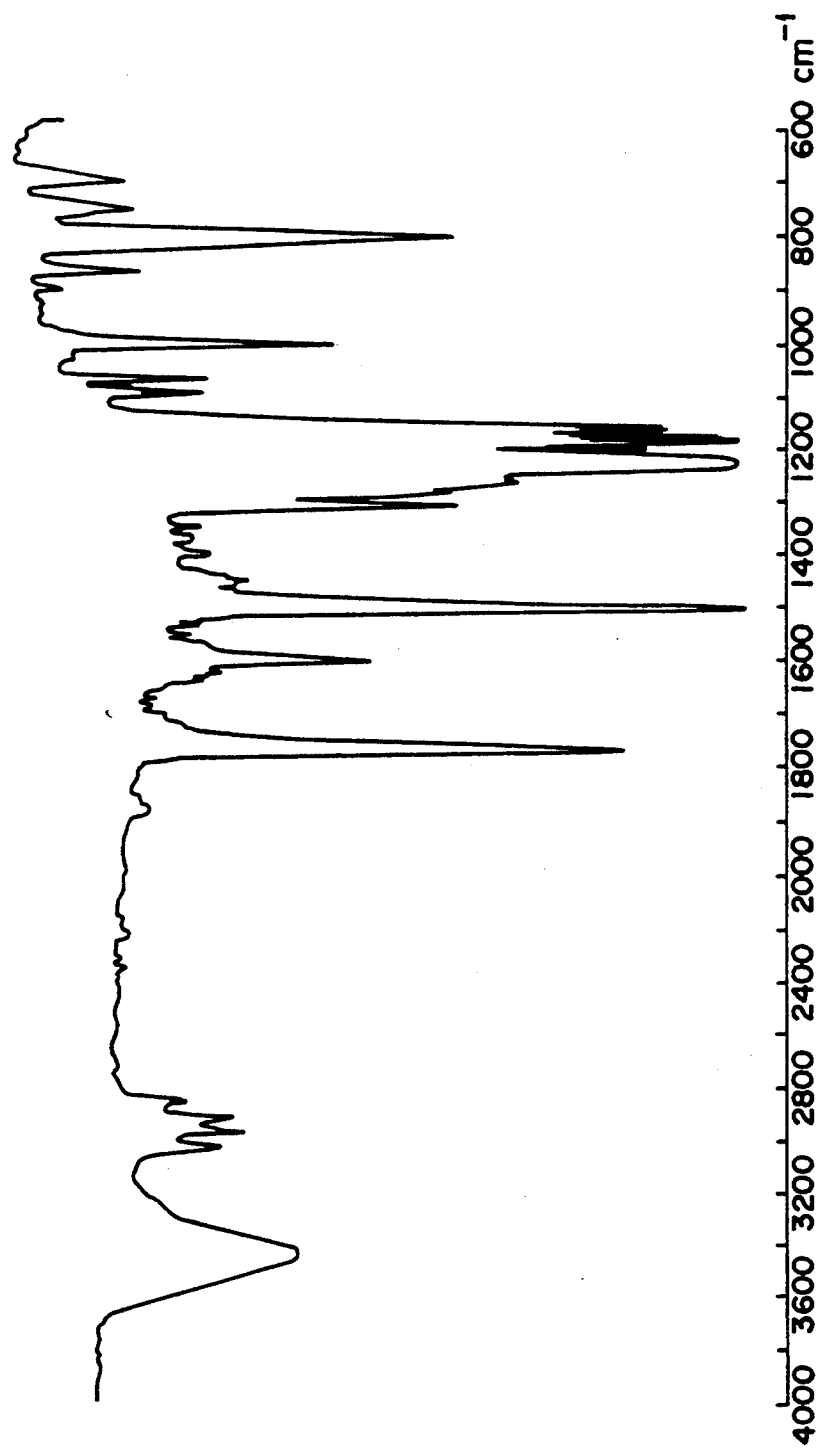
Figure 3:
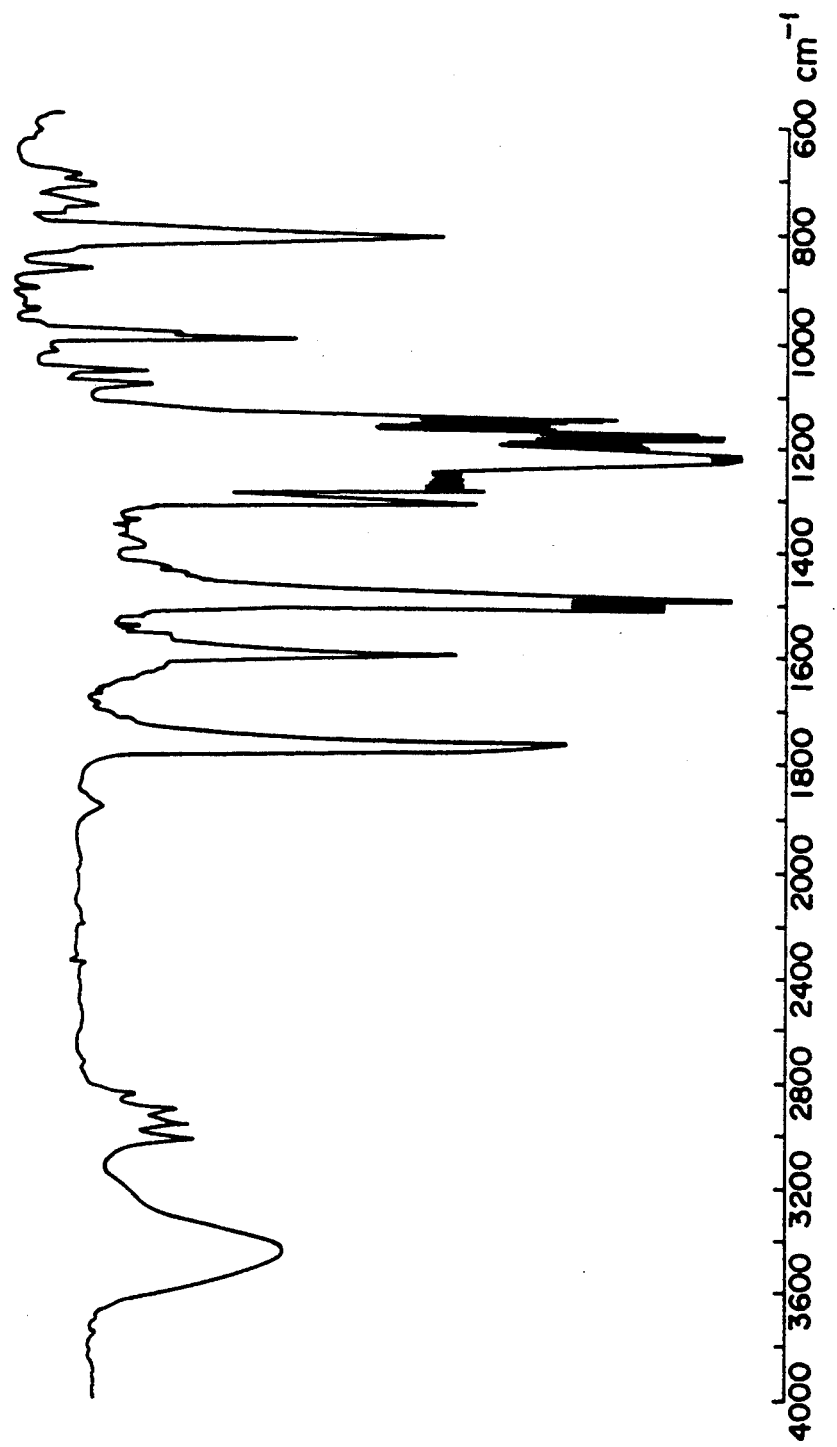
Figure 4:
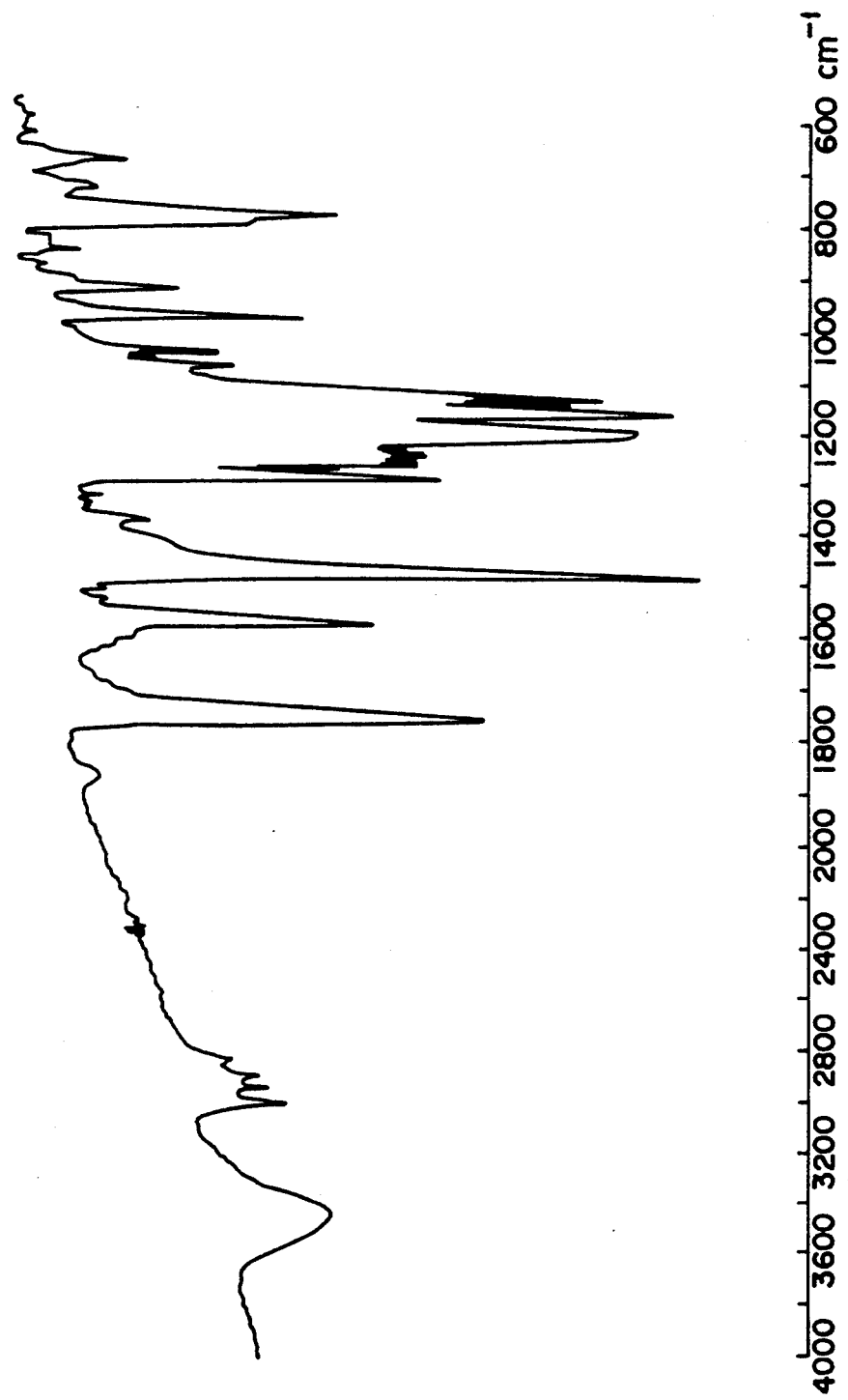
Figure 5:
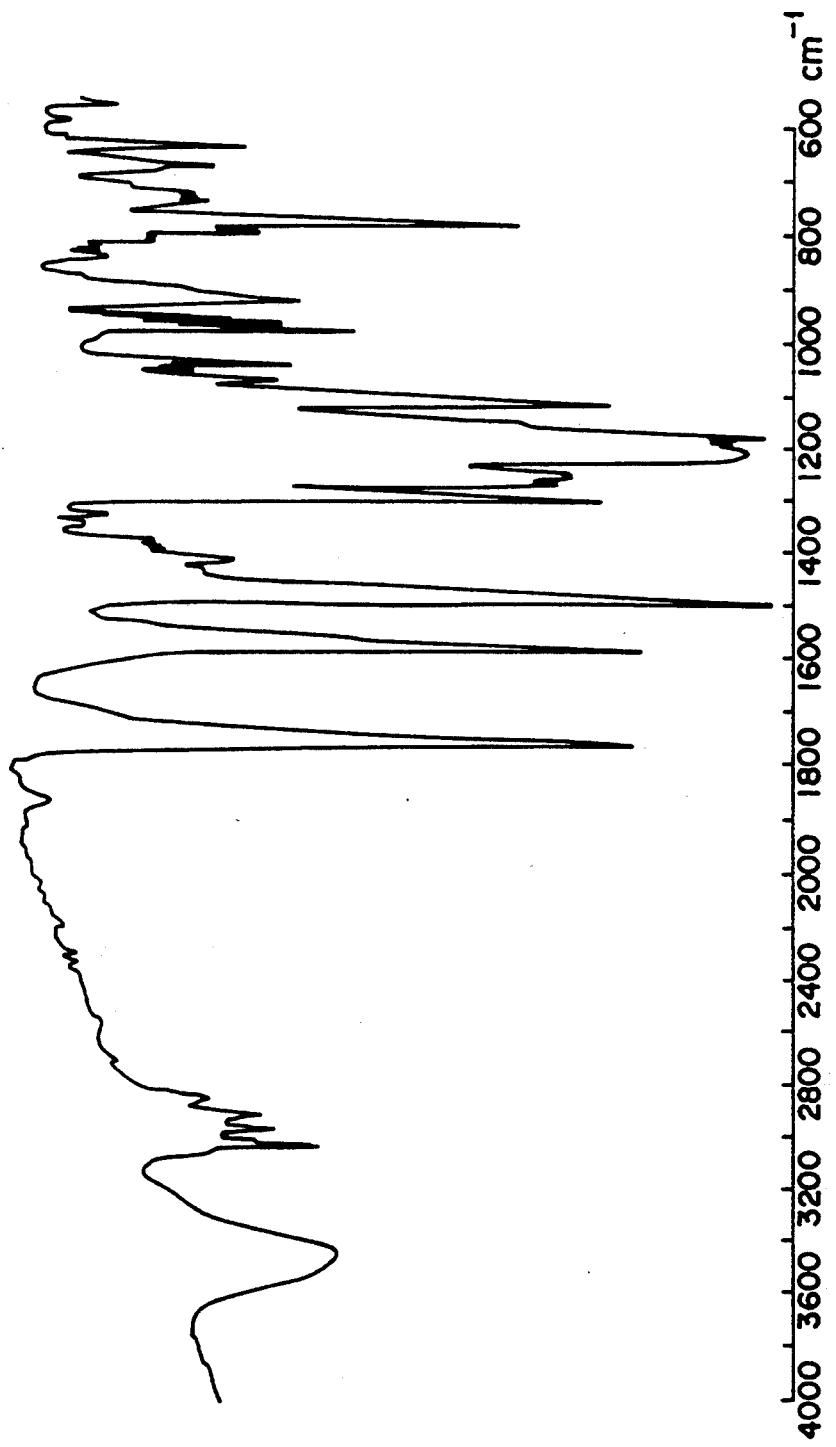
Figure 6:
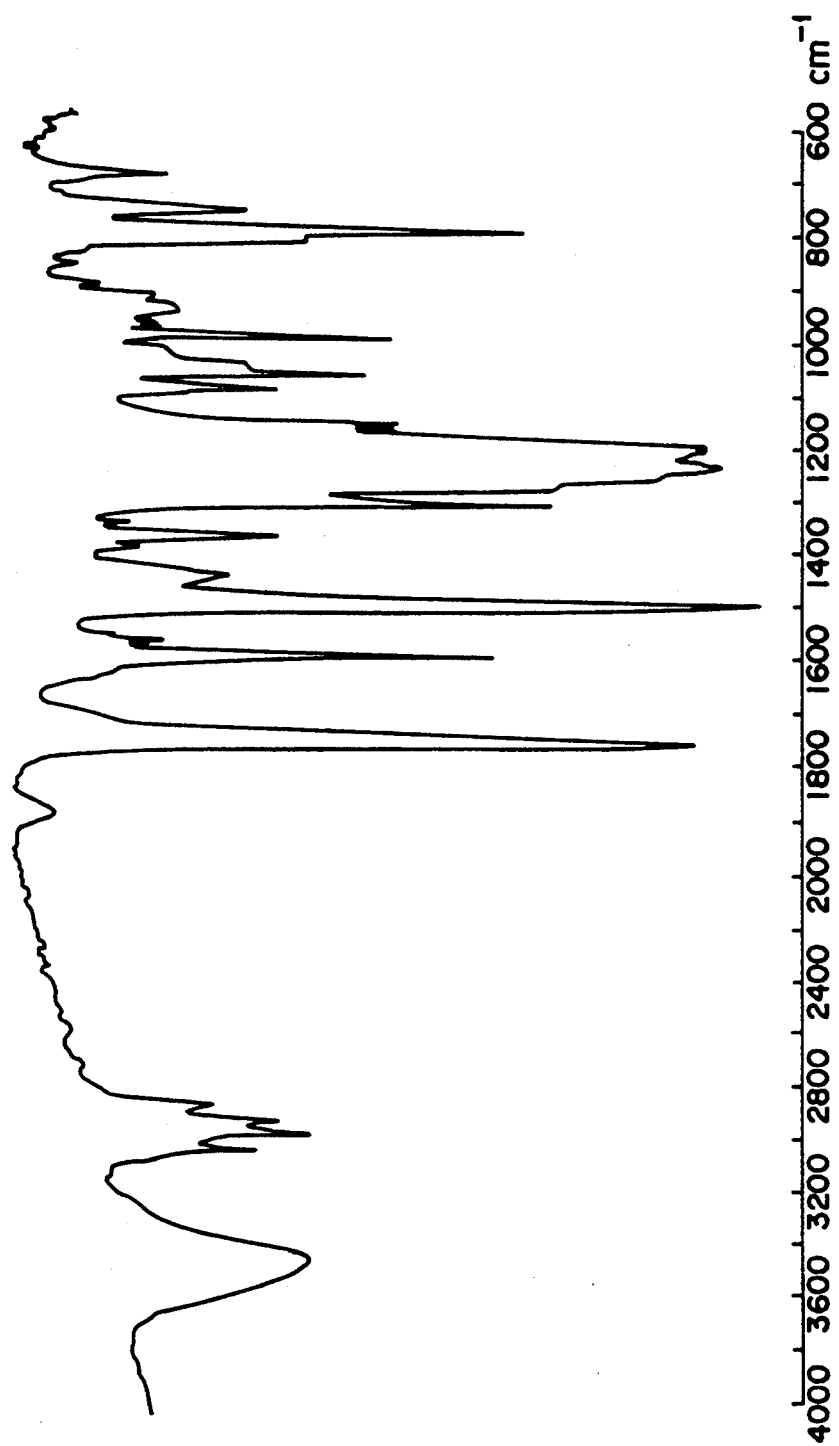
Figure 7:
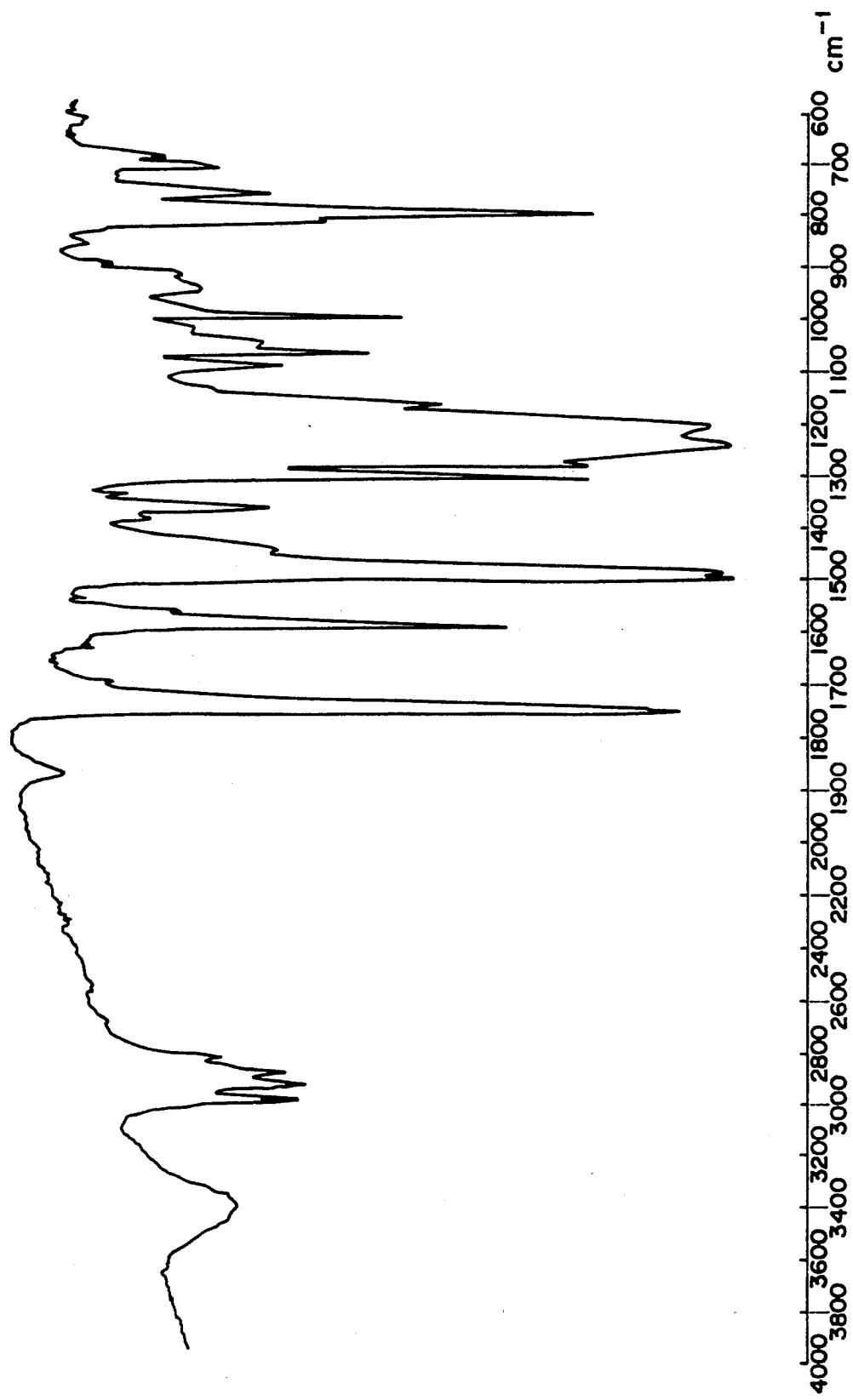
Figure 8:
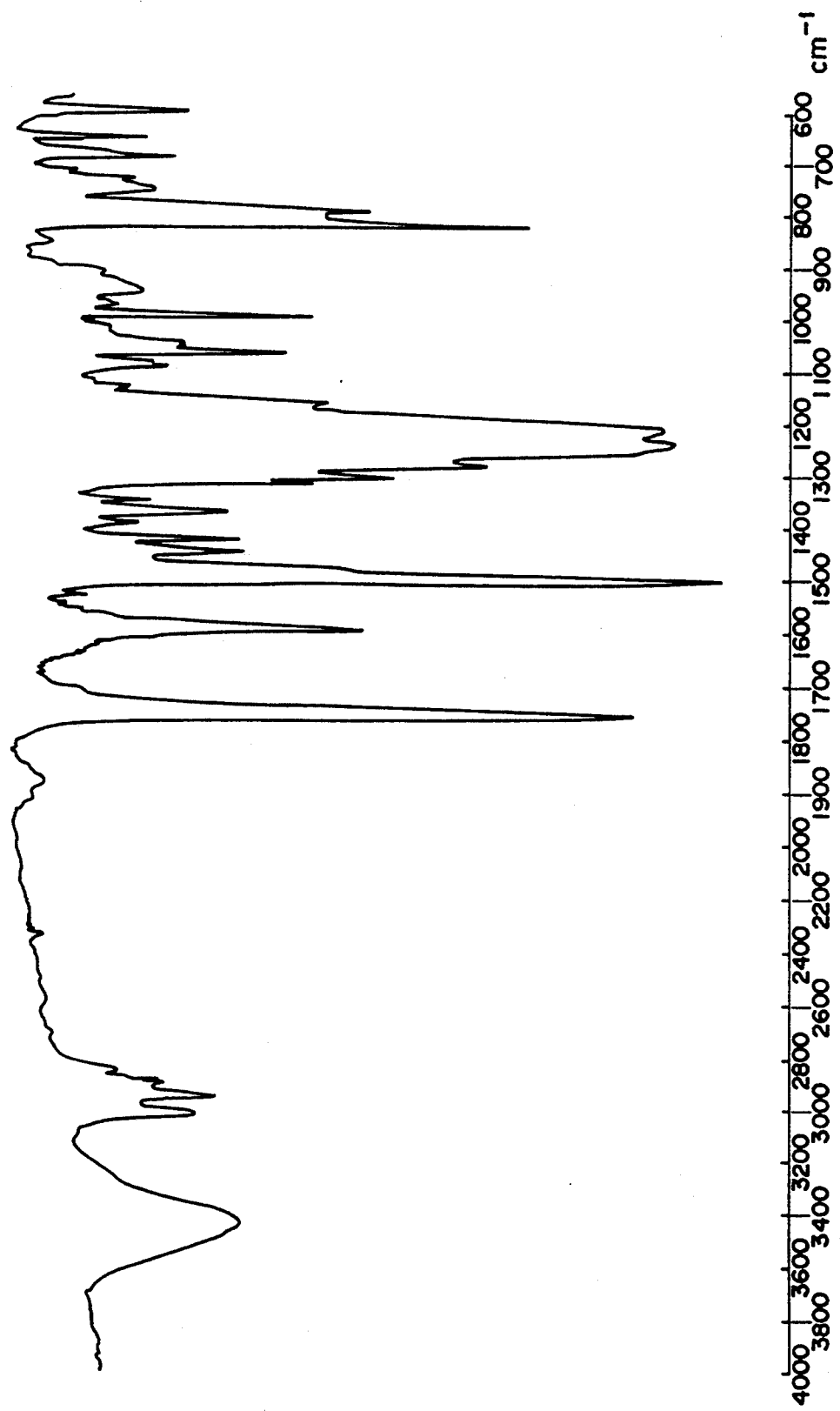
Figure 9:
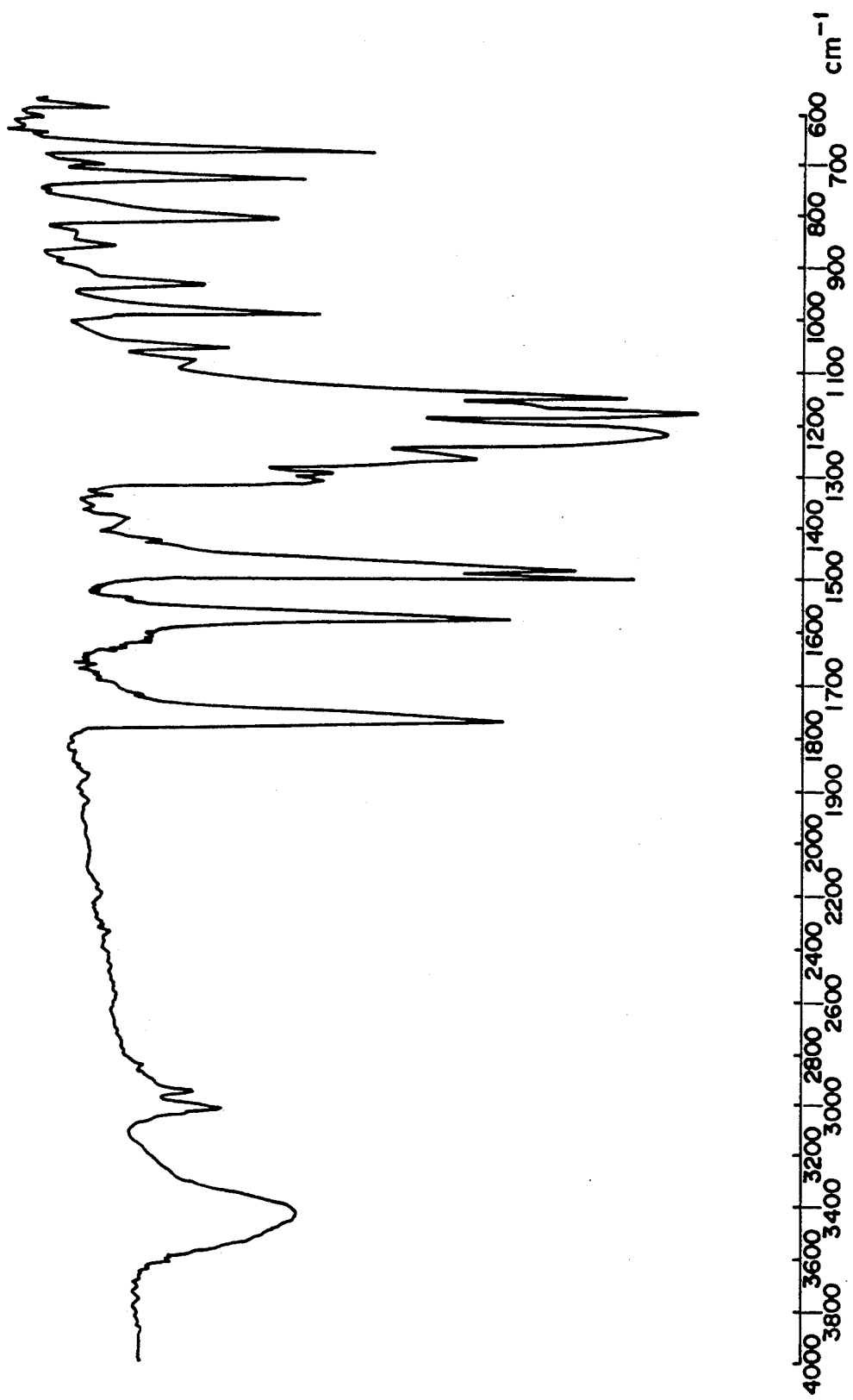
Figure 10:
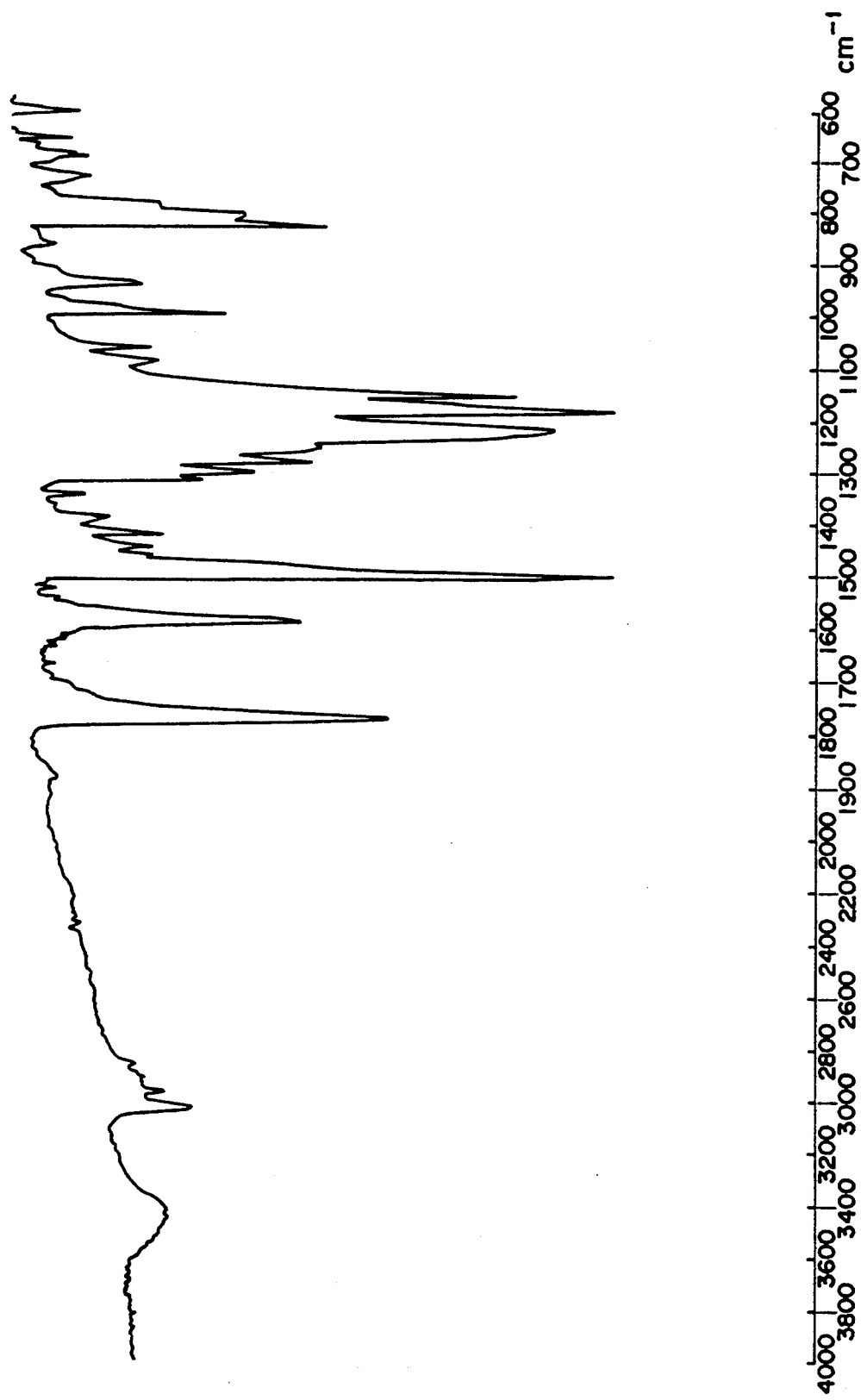
Figure 11:
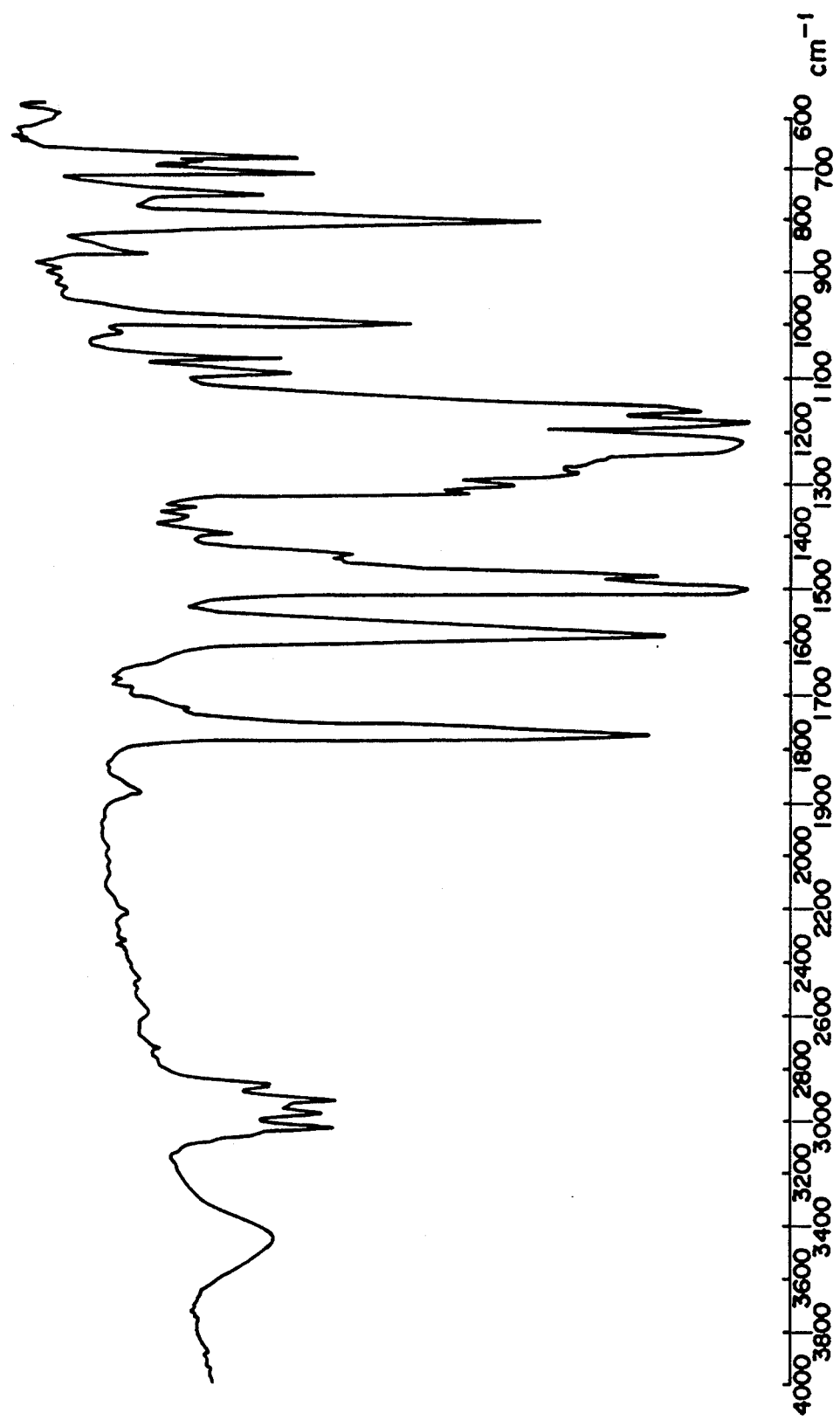
Figure 12:
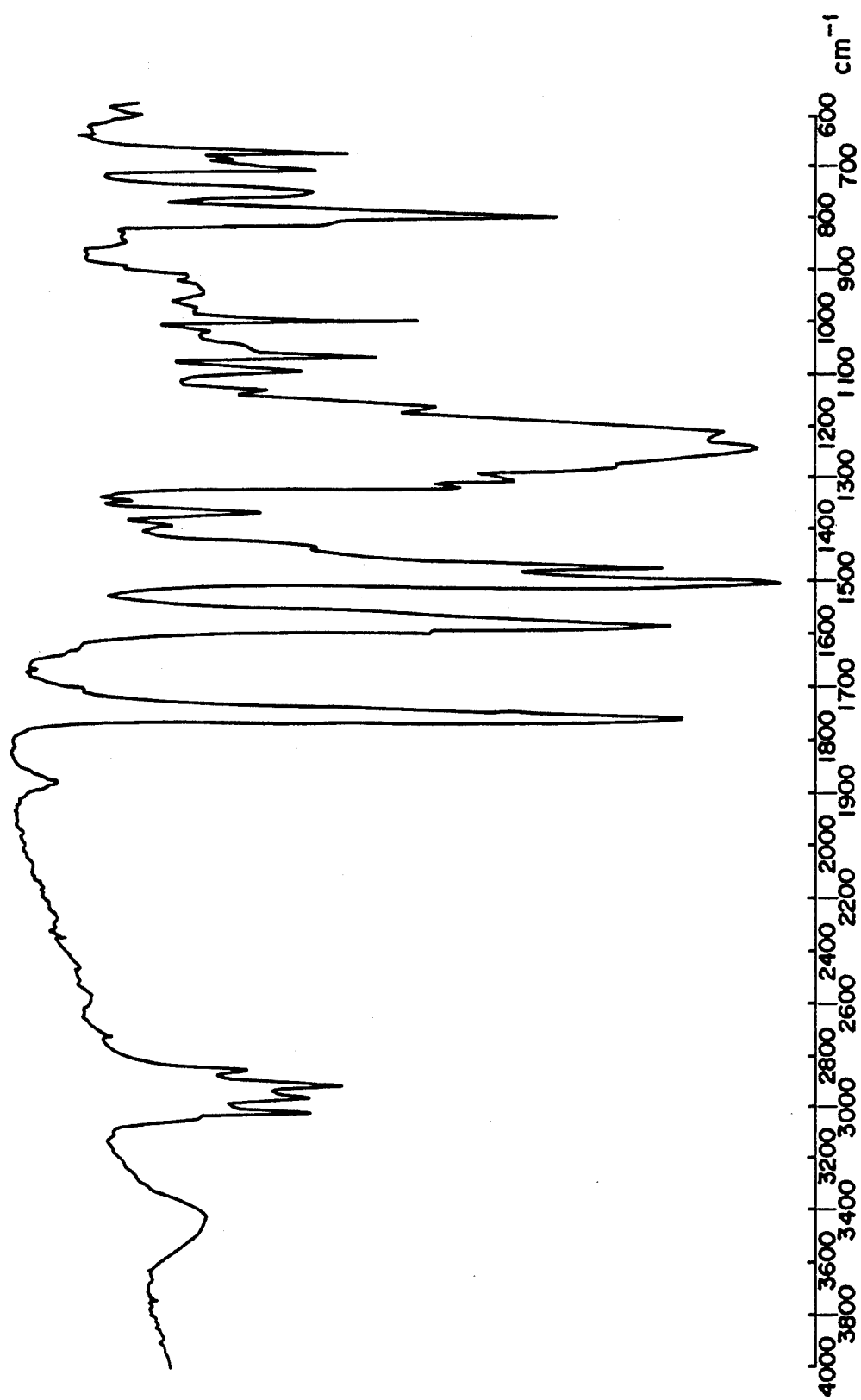

The alkyl group represented by $R^1$, $R^2$, $R^3$, and $R^4$ in formula (I) has 1 to 6 carbon atoms, preferably 1 to 4 carbon atoms.

Preferable examples of the alkyl group represented by $R^1$, $R^2$, $R^3$, and $R^4$ in formula (I) include methyl group, ethyl group, propyl group, and butyl group.

The alkoxyl group represented by $R^1$ in formula (I) has 1 to 6 carbon atoms, preferably 1 to 4 carbon atoms.

Preferable examples of the alkoxyl group represented by $R^1$ in formula (I) include methoxy group, ethoxy group, propoxy group, and butoxy group.

Specific examples of the halogen atom represented by $R^2$ in formula (I) include fluorine, chlorine, bromine and iodine.

The alkenyl group represented by $R^1$ in formula (I) has 1 to 6 carbon atoms, preferably 1 to 4 carbon atoms.

Specific examples of the alkenyl group represented by $R^1$ in formula (I) include ethenyl group, propynyl and 1,3-butadienyl group.

Specific examples of the aryl group represented by $R^1$, $R^2$, $R^3$, $R^4$, and $Ar^1$ in formula (I) include phenyl group, biphenylyl group, naphthyl group, anthryl group, and pyrenyl group.

A bivalent group of the above-mentioned aryl group can be employed as the arylene group represented by $Ar^2$ in formula (I).

Specific examples of the substituent for use in formula (I) are benzyl group, trifluoromethyl group, 2-methoxyethoxy group, styryl group, β-phenylstyryl group, 4-phenyl-1,3-butadienyl group, tolyl group, methoxyphenyl group, 4'-methyl-[1,1'-biphenyl]-4-yl group, methylphenylene group, and 3,3,'-dimethyl-[1,1'-biphenyl]-4,4'-diyl group.

Specific examples of the diamine compound according to the present invention are as follows:

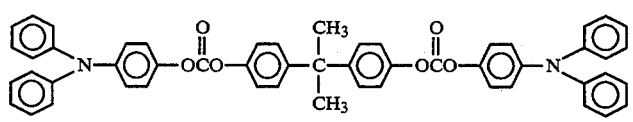

(Diamine Compound No. 1)

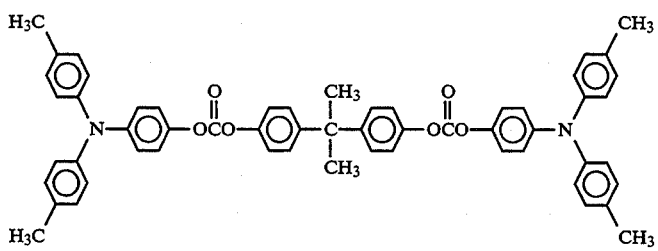

(Diamine Compound No. 2)

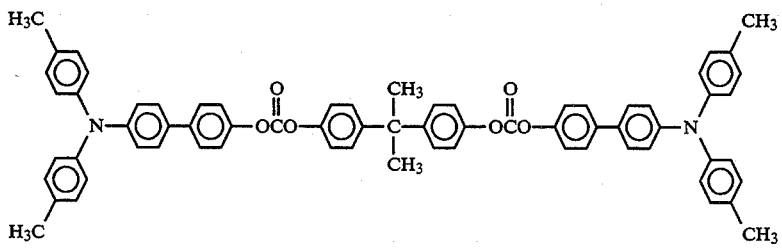

(Diamine Compound No. 3)

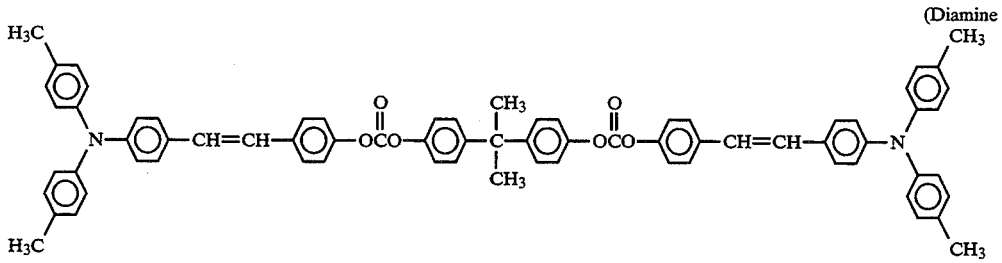

(Diamine Compound No. 4)

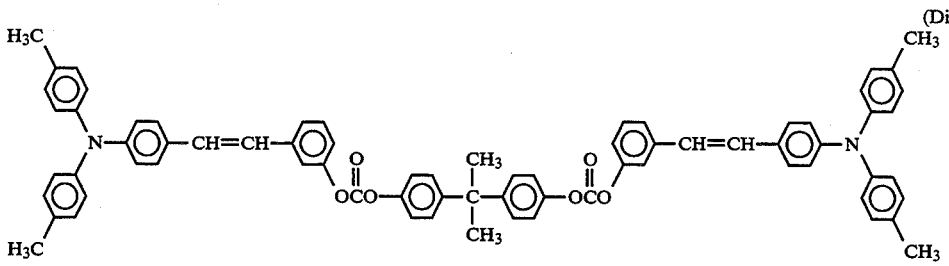

(Diamine Compound No. 5)

-continued
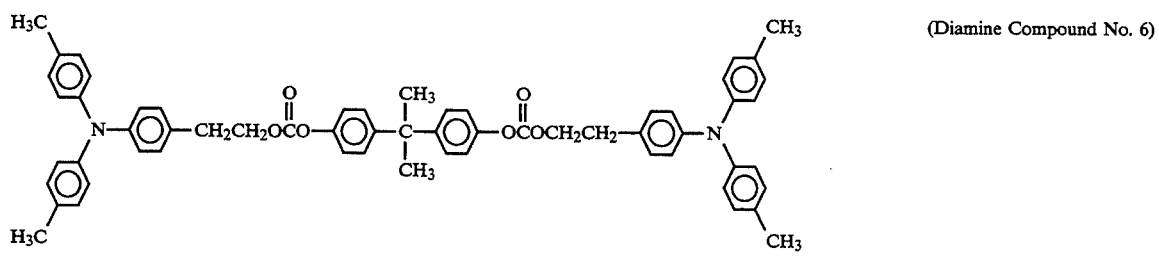
(Diamine Compound No. 6)
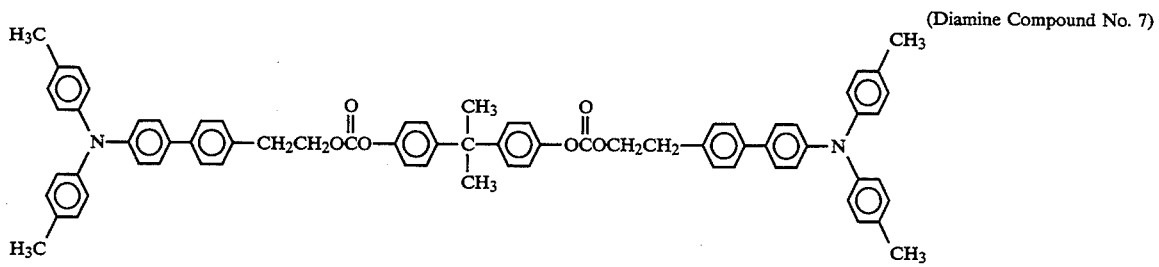
(Diamine Compound No. 7)
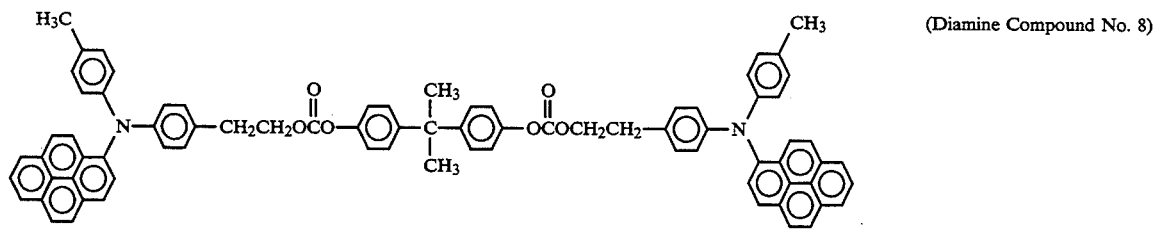
(Diamine Compound No. 8)
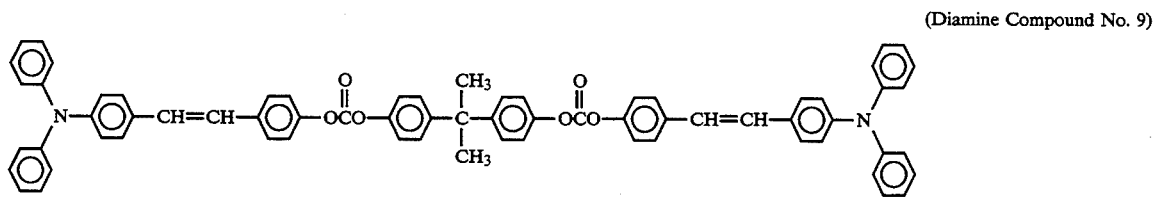
(Diamine Compound No. 9)
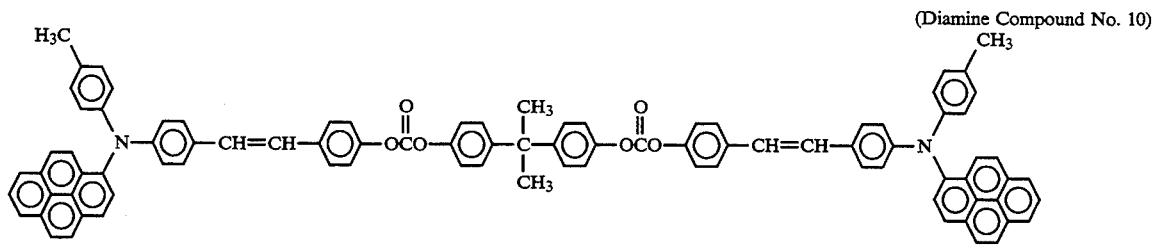
(Diamine Compound No. 10)
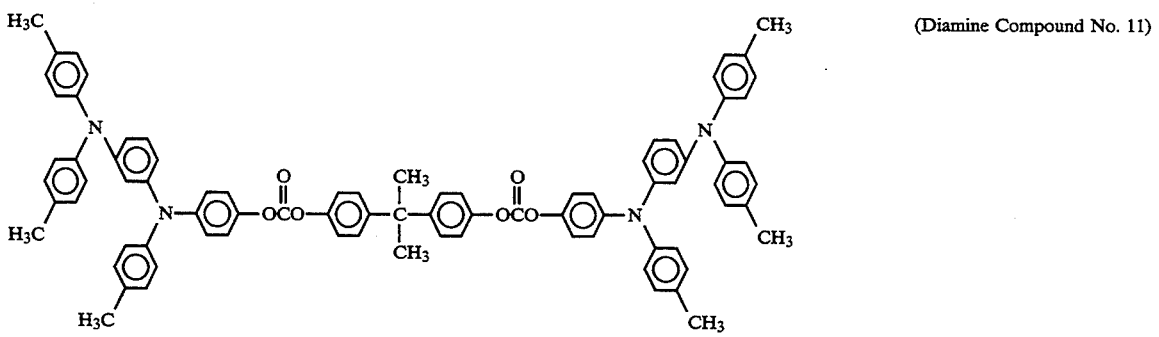
(Diamine Compound No. 11)

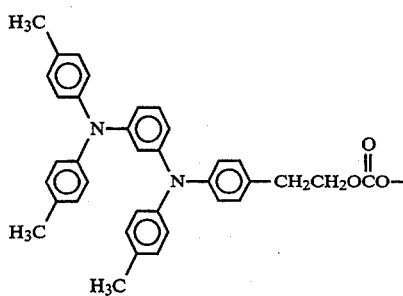 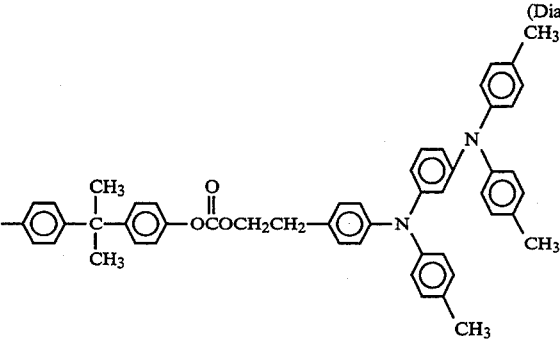

(Diamine Compound No. 12)

Among the above-mentioned diamine compounds of the present invention, the diamine compounds represented by the following formula (II) are preferable:

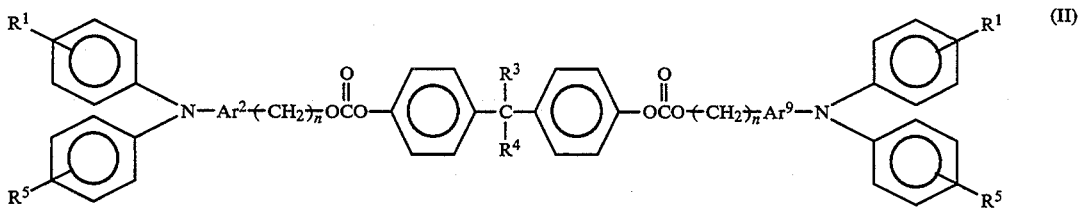

wherein $R^3$ and $R^4$ each is an alkyl group having 1 to 6 carbon atoms; $R^1$ and $R^5$ each is hydrogen or an alkyl group having 1 to 6 carbon atoms; $Ar^2$ is phenyl group or a bivalent group selected from the group consisting of a biphenyl group and a stilbene group; and n is an integer of 0 to 2.

The diamine compounds of formula (I) according to the present invention, which are novel compounds, can be synthesized by allowing a hydroxy compound of formula (III) to react with a bis(chloroformate) compound of formula (IV) in the presence of a solvent or without any solvent, using a catalyst. It is preferable to carry out the reaction at a temperature in the range from 0° to 150° C., more preferably in the range from 5° to 50° C. [Formula III]: hydroxy compound

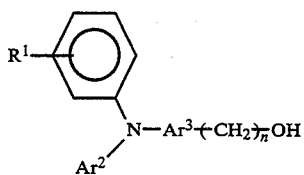

wherein $R^1$, $Ar^1$, $Ar^2$ and n are the same as those previously defined in formula (I). [Formula IV]: bis(chloroformate) compound

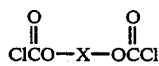

wherein X is the same as that previously defined in formula (I).

In the aforementioned reaction, nitrogen compounds such as diethylamine, triethylamine, tripropylamine, pyridine and quinoline; and hydroxides of alkali metals such as sodium hydroxide and potassium hydroxide are usable as the catalyst. The catalyst may be added to the reaction mixture in such an amount that can neutralize hydrogen chloride generated in the reaction. More specifically, the amount of the catalyst is preferably an equimolar quantity of the reaction group or up to three times the equimolar quantity thereof.

Examples of the solvent for use in the above-mentioned reaction are dichloromethane, chloroform, carbon tetrachloride, tetrahydrofuran, ethyl ether, toluene, xylene, acetone, methyl ethyl ketone, cyclohexane, and hexane.

The diamine compounds of formula (I) according to the present invention are remarkably effective as photoconductive materials in the electrophotographic photoconductor. The diamine compounds are optically or chemically sensitized with a sensitizer such as a dye or a Lewis acid. Therefore, these compounds are usable as charge transporting materials when contained in a photoconductive layer of the electrophotographic photoconductor, especially of a function-separating type electrophotographic photoconductor comprising a charge generation layer which comprises an organic or inorganic pigment as a charge generating material and a charge transport layer.

Specific examples of the sensitizer to be used together with the diamine compound of the present invention are as follows: triarylmethane dyes such as Methyl Violet and Crystal Violet; xanthene dyes such as Rose Bengale, Erythrosin and Rhodamine; thiazine dyes such as Methylene Blue; and 2,4,7-trinitro-9-fluorenone and 2,4-dinitro-9-fluorenone.

Specific examples of the charge generating material for use in the electrophotographic photoconductor when the diamine compound of the present invention is used as the charge transporting material therein are as follows:

(1) Organic pigments: azo pigments such as C. I. Pigment Blue 25 (C.I. 21180), C.I. Pigment Red 41 (C.I. 21200) and C.I. Pigment Red 3 (C.I. 45210) phthalocyanine pigments such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B (made by Bayer Co., Ltd.) and Indanthrene Scarlet R (made by Bayer Co., Ltd.).

(2) Inorganic pigments: selenium, selenium-tellurium, cadmium sulfide, and α-silicon (amorphous silicon).

1 with the following formula was obtained as colorless crystals in the form of plates. The yield was 2.52 g (52.3%).

The melting point of the above obtained diamine compound No. 1 was 204.0° to 205.5° C.

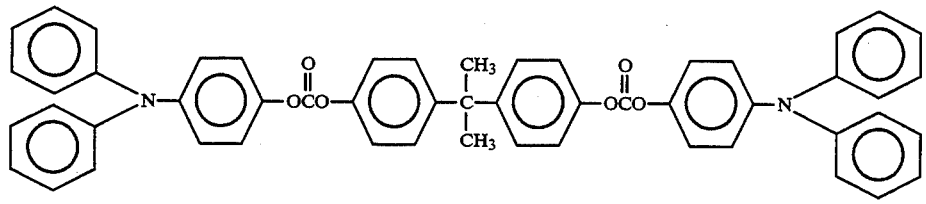

Other features of this invention will become apparent in the course of the following description of exemplary embodiments, which are given for illustration of the invention and are not intended to be limiting thereof.

EXAMPLE 1

3.14 g (12.0 mmol) of 4-hydroxytriphenylamine and 1.86 g (14.4 mmol) of quinoline were dissolved in 20 ml of dried dichloromethane. To this solution, 20 ml of dried dichloromethane in which 2.12 g (6.00 mmol) of 4,4'-isopropylidenediphenolbis(chloroformate) were dissolved were added dropwise in a stream of nitrogen at room temperature over a period of 15 minutes.

The reaction mixture was stirred at 40° C. for 4 hours. Then, the reaction mixture was washed with water three times, and then with a saturated aqueous solution of sodium chloride once, using a separating funnel. Thereafter, the reaction mixture was dried over magnesium sulfate and concentrated under reduced pressure to yield a green oily material. The resulting product was chromatographed on a silica gel column using a mixed solvent of toluene and n-hexane with a volume ratio of 3:1 as an eluting solution. Then, the compound thus obtained was recrystallized from a mixed solvent of toluene and n-hexane, so that a diamine compound No.

The results of the elemental analysis of the diamine compound No. 1 were as follows:

|  | C(%) | H(%) | N(%) |
| --- | --- | --- | --- |
| Found | 79.56 | 4.96 | 3.25 |
| Calculated | 79.28 | 5.27 | 3.49 |

The above calculation was based on the formula for $C_{53}H_{42}N_2O_6$.

FIG. 1 shows an infrared spectrum of the diamine compound No. 1, taken by use of a KBr tablet.

EXAMPLES 2 to 12

The procedure for preparation of the diamine compound No. 1 in Example 1 was repeated except that 4-hydroxytriphenylamine for use in Example 1 was separately changed, so that diamine compounds Nos. 2 to 12 according to the present invention were obtained.

The structural formula, the melting point, and the results of the elemental analysis of each diamine compound are shown in Table 1.

FIGS. 2 through 12 respectively show infrared spectra of the above diamine compounds Nos. 2 to 12, taken by use of a KBr tablet.

TABLE 1

| Example No. | Structural Formula | Melting Point (°C.) (Solvent in Recrystallization) | Elemental Analysis (%) C: Found (Calculated) | H: Found (Calculated) | N: Found (Calculated) |
|---|---|---|---|---|---|
| Ex. 2 | | 138.5–141.5 (Toluene-n-hexane) | 79.81 (79.69) | 5.72 (5.87) | 3.18 (3.25) |
| Ex. 3 | | 183.0–184.5 (Toluene-n-hexane) | 81.90 (81.95) | 5.77 (5.78) | 2.65 (2.77) |
| Ex. 4 | | Amorphous (—) | 82.71 (82.46) | 5.92 (5.88) | 2.67 (2.63) |
| Ex. 5 | | Amorphous (—) | 82.91 (82.46) | 6.07 (5.88) | 2.58 (2.63) |

TABLE 1-continued

| Example No. | Structural Formula | Melting Point (°C.) (Solvent in Recrystallization) | Elemental Analysis (%) | | |
|---|---|---|---|---|---|
| | | | C: Found (Calculated) | H: Found (Calculated) | N: Found (Calculated) |
| Ex. 6 | [structure] | Amorphous (—) | 79.72 (80.06) | 6.28 (6.39) | 2.92 (3.06) |
| Ex. 7 | [structure] | Amorphous (—) | 82.51 (82.15) | 6.41 (6.23) | 2.65 (2.63) |
| Ex. 8 | [structure] | 147–172 (Ethylacetate) | 83.65 (83.57) | 5.61 (5.51) | 2.49 (2.47) |
| Ex. 9 | [structure] | Amorphous (—) | 82.39 (82.28) | 5.47 (5.40) | 2.71 (2.78) |

TABLE 1-continued

| Example No. | Structural Formula | Melting Point (°C.) (Solvent in Recrystallization) | Elemental Analysis (%) | | |
|---|---|---|---|---|---|
| | | | C: Found (Calculated) | H: Found (Calculated) | N: Found (Calculated) |
| Ex. 10 | [structure with pyrenyl and tolylamine groups] | Amorphous (—) | 85.41 (85.15) | 5.43 (5.18) | 2.33 (2.18) |
| Ex. 11 | [structure with di(tolyl)amino groups] | Amorphous (—) | 81.78 (81.61) | 6.01 (5.94) | 4.57 (4.59) |
| Ex. 12 | [structure with di(tolyl)amino groups and OCOCH$_2$CH$_2$ linker] | Amorphous (—) | 81.54 (81.79) | 6.60 (6.31) | 4.26 (4.39) |

Application Example 7.5 parts by weight of a bisazo compound of formula (A) serving as a charge generating material and 500 parts by weight of a 0.5% tetrahydrofuran solution of a polyester resin (Trademark "Vylon 200" made by Toyobo Company, Ltd.) were dispersed and ground in a ball mill. [Formula A]: bisazo compound

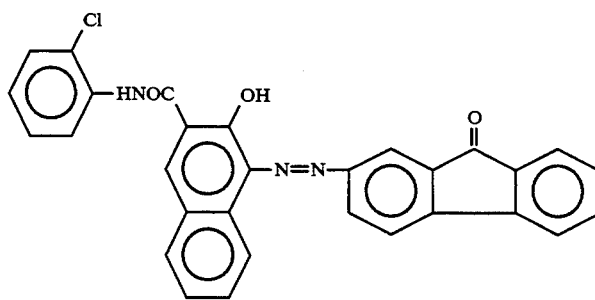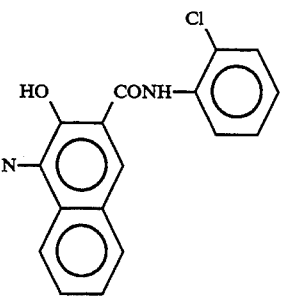

The thus prepared dispersion was coated on an aluminum surface of an aluminum-deposited polyester film serving as an electroconductive substrate by a doctor blade, and dried at room temperature, so that a charge generation layer with a thickness of about 1 μm was formed on the electroconductive substrate.

One part by weight of the diamine compound No. 3 serving as a charge transporting material obtained in Example 3 was dissolved in a resin solution of 8 parts by weight of tetrahydrofuran and 1 part by weight of a polycarbonate resin (Trademark "Panlite K-1300" made by Teijin Limited) to prepare a coating liquid for a charge transport layer. This liquid was coated on the previously formed charge generation layer by a doctor blade, and dried at 80° C. for 2 minutes and then at 120° C. for 5 minutes, so that a charge transport layer with a thickness of about 20 μm was formed on the charge generation layer. Thus, an electrophotographic photoconductor A was prepared.

To evaluate the photosensitivity in the visible light range, the above prepared lamination-type electrophotographic photoconductor A was charged under application of −6 kV of corona charge for 20 seconds, using a commercially available electrostatic copying sheet testing apparatus ("Paper Analyzer Model SP-428" made by Kawaguchi Electro Works Co., Ltd.). The initial surface potential Vm (V) of the photoconductor A was measured after charging. Then, the electrophotographic photoconductor A was allowed to stand in the dark for 20 seconds without applying any charge thereto, and the surface potential Vo (V) of the photoconductor A was measured. Thereafter, the photoconductor A was illuminated by a tungsten lamp in such a manner that the illuminance on the illuminated surface of the photoconductor was 4.5 lux, and the exposure $E_{\frac{1}{2}}$ (lux·sec) required to reduce the initial surface potential Vo (V) to $\frac{1}{2}$ thereof was measured.

Furthermore, the surface potential Vr (V) of the photoconductor A was measured after illuminated by the tungsten lamp for 30 seconds.

The results are shown in Table 2.

TABLE 2

| | Vm (V) | Vo (V) | Vr (V) | E1/2 |
|---|---|---|---|---|
| Photoconductor A | −1615 | −1456 | 0 | 1.55 |

The diamine compounds of formula (I) according to the present invention are remarkably effective as photoconductive materials in the electrophotographic photoconductor. The diamine compounds are optically or chemically sensitized with a sensitizer such as a dye or a Lewis acid. Therefore, these compounds are usable as charge transporting materials when contained in a photoconductive layer of the electrophotographic photoconductor, especially of a lamination-type electrophotographic photoconductor comprising a charge generation layer which comprises an organic or inorganic pigment as a charge generating material and a charge transport layer.

Japanese Patent Application 5-340078 filed on Dec. 7, 1993 is hereby incorporated by reference.

What is claimed is:

1. An electrophotographic photoconductor comprising an electroconductive support and photoconductive element thereon, said photoconductive element including a charge transport material comprising a diamine compound having the formula (I):

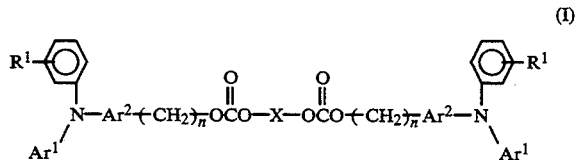

wherein $R^1$ is hydrogen, an alkyl group having 1 to 6 carbon atoms which may have a substituent, an alkoxyl group having 1 to 6 carbon atoms which may have a substituent, an aryl group which may have a substituent, or an alkenyl group having 1 to 6 carbon atoms which may have a substituent; $AR^1$ is an aryl group which may have a substituent; $Ar^2$ is a bivalent group selected from the group consisting of an arylene group and a stilbene group, which may have a substituent; n is an integer of 0 to 2; and X is a group selected from the group consisting of:

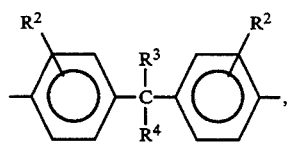

-continued

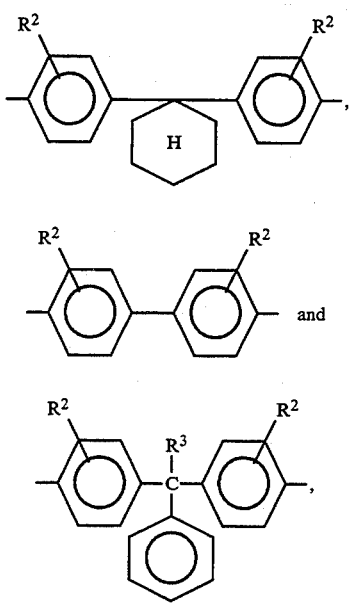

in which R² is hydrogen, an alkyl group having 1 to 6 carbon atoms which may have a substituent, an aryl group or a halogen; R³ and R⁴ each is an alkyl group having 1 to 6 carbon atoms or an aryl group.

2. An electrophotographic photoconductor as set forth in claim 1, wherein said photoconductor is a layered material comprising a charge generation layer containing a charge generating material and a charge transport layer containing said charge transport material.

3. An electrophotographic photoconductor as set forth in claim 2, wherein said charge generating layer comprises an organic or inorganic pigment.

4. An electrophotographic photoconductor as set forth in claim 1 wherein said alkyl group represented by R¹, R², R³, and R⁴ in the diamine of formula (I) is selected from the group consisting of methyl group, ethyl group, propyl group, and butyl group.

5. An electrophotographic photoconductor as set forth in claim 1, wherein said alkoxyl group represented by R¹ in the diamine of formula (I) is selected from the group consisting of methoxy group, ethoxy group, propoxy group, and butoxy group.

6. An electrophotographic photoconductor as set forth in claim 1, wherein said halogen atom represented by R², in the diamine of formula (I) is selected from the group consisting of fluorine, chlorine, bromine and iodine.

7. The electrophotographic photoconductor as set forth in claim 1, wherein said alkenyl group represented by R¹, in the diamine of formula (I) is selected from the group consisting of ethenyl group, propynyl and 1,3-butadienyl group.

8. The electrophotographic photoconductor as set forth in claim 1, wherein said aryl group represented by R¹, R², R³, and R⁴ and Ar¹ in the diamine of formula (I) is selected from the group consisting of phenyl group, biphenylyl group, naphthyl group, anthryl group, and pyrenyl group.

9. The electrophotographic photoconductor as set forth in claim 1, wherein said substituents for use in the diamine of formula (1) is selected from the group consisting of benzyl group, trifluoromethyl group, 2-methoxyethoxy group, styryl group β-phenylstyryl group, 4-phenyl-1,3 butadienyl group, tolyl group, methoxyphenyl group, 4'-methyl-[1,1'-biphenyl]-4,4'-diyl group.

* * * * *

UNITED STATES PATENT AND TRADEMARK OFFICE
CERTIFICATE OF CORRECTION

PATENT NO.    : 5,434,028
DATED:        : JULY 18, 1995
INVENTOR(S)   : Tomoyuki SHIMADA et al It is certified that error appears in the above-identified patent and that said Letters patent is hereby corrected as shown below:

Column 1, line 44,    "invention is to" should read --invention to--.

Column 9, line 27, "were" should read --when--.

Column 18, line 55, "AR$^1$" should read --Ar$^1$--.

Signed and Sealed this

Fourth Day of August, 1998

*Attest:*

BRUCE LEHMAN

*Attesting Officer*       *Commissioner of Patents and Trademarks*